(12) United States Patent
Weitzner et al.

(10) Patent No.: US 8,414,505 B1
(45) Date of Patent: Apr. 9, 2013

(54) CATHETER DRIVER SYSTEM

(75) Inventors: Barry Weitzner, Acton, MA (US); Brian Murphy, Watertown, MA (US)

(73) Assignee: Hansen Medical, Inc., Mountain View, CA (US)

( * ) Notice: Subject to any disclaimer, the term of this patent is extended or adjusted under 35 U.S.C. 154(b) by 2634 days.

(21) Appl. No.: 10/270,743

(22) Filed: Oct. 11, 2002

Related U.S. Application Data

(63) Continuation-in-part of application No. 10/216,067, filed on Aug. 8, 2002, now abandoned, and a continuation-in-part of application No. 10/023,024, filed on Nov. 16, 2001, now abandoned, and a continuation-in-part of application No. 10/011,371, filed on Nov. 16, 2001, now Pat. No. 7,090,683, and a continuation-in-part of application No. 10/011,449, filed on Nov. 16, 2001, now abandoned, and a continuation-in-part of application No. 10/010,150, filed on Nov. 16, 2001, now Pat. No. 7,214,230, and a continuation-in-part of application No. 10/022,038, filed on Nov. 16, 2001, now abandoned, and a continuation-in-part of application No. 10/012,586, filed on Nov. 16, 2001, now Pat. No. 7,371, 210.

(60) Provisional application No. 60/332,287, filed on Nov. 21, 2001, provisional application No. 60/313,497, filed on Aug. 21, 2001, provisional application No. 60/269,200, filed on Feb. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/293,346, filed on May 24, 2001.

(51) Int. Cl.
*A61B 5/00* (2006.01)

(52) U.S. Cl.
USPC .......................................................... 600/585

(58) Field of Classification Search .................. 600/585, 600/385, 146, 151, 141; 604/164.09, 164.12, 604/158
See application file for complete search history.

(56) References Cited

U.S. PATENT DOCUMENTS 3,414,137 A 12/1968 Fortin
4,294,254 A 10/1981 Chamness
(Continued)

FOREIGN PATENT DOCUMENTS

EP 0 683 016 A1 5/1995
EP 0776738 4/1997
(Continued)

OTHER PUBLICATIONS

Ikuta, et al., "Shape Memory Alloy Servo Actuator System With Electric Resistance Feedback and Application for Active Endoscope", 1988 IEEE, CH2555-1/88/0000/0427-430.

(Continued)

*Primary Examiner* — Brian Szmal
*Assistant Examiner* — Fangemonique Smith
(74) *Attorney, Agent, or Firm* — Vista IP Law Group LLP

(57) ABSTRACT

An apparatus for performing medical procedures on an anatomical body includes an extension with an element near its distal end to be extended into the body, and a driver that moves the extension axially into the body, and that causes flexure of the distal end of the extension. The movement and flexure of the extension is driven by the driver from the proximal end of the extension, and an electronic controller directs the operation of the driver.

19 Claims, 7 Drawing Sheets

U.S. PATENT DOCUMENTS

| | | | |
|---|---|---|---|
| 4,604,016 A | 8/1986 | Joyce | |
| 4,654,024 A | 3/1987 | Crittenden et al. | |
| 4,702,250 A | 10/1987 | Ovil et al. | |
| 4,750,475 A | 6/1988 | Yoshihashi | |
| 4,853,874 A | 8/1989 | Iwamoto et al. | |
| 4,941,454 A | 7/1990 | Wood et al. | |
| 4,977,886 A | 12/1990 | Takehana et al. | |
| 4,979,949 A | 12/1990 | Matsen, III et al. | |
| 5,047,011 A * | 9/1991 | Caron et al. | 604/29 |
| 5,052,402 A | 10/1991 | Bencini et al. | |
| 5,072,361 A | 12/1991 | Davis et al. | |
| 5,078,140 A | 1/1992 | Kwoh | |
| 5,084,054 A | 1/1992 | Bencini et al. | |
| 5,086,401 A | 2/1992 | Glassman et al. | |
| 5,116,180 A | 5/1992 | Fung et al. | |
| 5,154,717 A | 10/1992 | Matsen, III et al. | |
| 5,172,700 A | 12/1992 | Bencini et al. | |
| 5,174,276 A | 12/1992 | Crockard | |
| 5,174,278 A | 12/1992 | Babkow | |
| 5,184,601 A | 2/1993 | Putman | |
| 5,217,003 A | 6/1993 | Wilk | |
| 5,236,432 A | 8/1993 | Matsen, III et al. | |
| 5,238,002 A | 8/1993 | Devlin et al. | |
| 5,238,005 A | 8/1993 | Imran | |
| 5,271,381 A | 12/1993 | Ailenger et al. | |
| 5,287,861 A | 2/1994 | Wilk | |
| 5,295,958 A | 3/1994 | Shturman | |
| 5,299,288 A | 3/1994 | Glassman et al. | |
| 5,339,799 A | 8/1994 | Kami et al. | |
| 5,346,498 A * | 9/1994 | Greelis et al. | 606/108 |
| 5,347,987 A | 9/1994 | Feldstein et al. | |
| 5,350,355 A | 9/1994 | Sklar | |
| 5,368,015 A | 11/1994 | Wilk | |
| 5,372,147 A | 12/1994 | Lathrop, Jr. et al. | |
| 5,382,685 A | 1/1995 | Klein et al. | |
| 5,382,885 A | 1/1995 | Salcudean et al. | |
| 5,389,100 A | 2/1995 | Bacich et al. | |
| 5,397,323 A | 3/1995 | Taylor et al. | |
| 5,398,691 A | 3/1995 | Martin et al. | |
| 5,402,801 A | 4/1995 | Taylor | |
| 5,409,019 A | 4/1995 | Wilk | |
| 5,410,638 A | 4/1995 | Colgate et al. | |
| 5,417,210 A | 5/1995 | Funda et al. | |
| 5,429,144 A | 7/1995 | Wilk | |
| 5,447,149 A | 9/1995 | Kikawada et al. | |
| 5,480,422 A | 1/1996 | Ben-Haim | |
| 5,497,784 A | 3/1996 | Imran | |
| 5,515,478 A | 5/1996 | Wang | |
| 5,520,644 A | 5/1996 | Imran | |
| 5,524,180 A | 6/1996 | Wang et al. | |
| 5,527,279 A | 6/1996 | Imran | |
| 5,540,649 A | 7/1996 | Bonnell et al. | |
| 5,553,198 A | 9/1996 | Wang et al. | |
| 5,572,999 A | 11/1996 | Funda et al. | |
| 5,606,979 A | 3/1997 | Hodgson | |
| 5,618,294 A | 4/1997 | Aust et al. | |
| 5,624,398 A | 4/1997 | Smith et al. | |
| 5,626,553 A | 5/1997 | Frassica et al. | |
| 5,626,595 A | 5/1997 | Sklar et al. | |
| 5,631,973 A | 5/1997 | Green | |
| 5,632,758 A | 5/1997 | Sklar | |
| 5,634,897 A | 6/1997 | Dance et al. | |
| 5,636,634 A | 6/1997 | Kordis et al. | |
| 5,649,956 A | 7/1997 | Jensen et al. | |
| 5,657,429 A | 8/1997 | Wang et al. | |
| 5,667,476 A | 9/1997 | Frassica et al. | |
| 5,674,279 A | 10/1997 | Wright et al. | |
| 5,749,362 A | 5/1998 | Funda et al. | |
| 5,754,741 A | 5/1998 | Wang et al. | |
| 5,759,153 A | 6/1998 | Webler et al. | |
| 5,762,458 A | 6/1998 | Wang et al. | |
| 5,784,542 A | 7/1998 | Ohm et al. | |
| 5,792,135 A | 8/1998 | Madhani et al. | |
| 5,800,333 A | 9/1998 | Liprie | |
| 5,800,423 A | 9/1998 | Jensen | |
| 5,807,377 A | 9/1998 | Madhani et al. | |
| 5,808,665 A | 9/1998 | Green | |
| 5,810,880 A | 9/1998 | Jensen et al. | |
| 5,814,038 A | 9/1998 | Jensen et al. | |
| 5,815,640 A | 9/1998 | Wang et al. | |
| 5,821,920 A | 10/1998 | Rosenberg et al. | |
| 5,823,993 A | 10/1998 | Lemelson | |
| 5,825,982 A | 10/1998 | Wright et al. | |
| 5,827,313 A | 10/1998 | Ream | |
| 5,828,197 A | 10/1998 | Martin et al. | |
| 5,833,656 A | 11/1998 | Smith et al. | |
| 5,845,646 A | 12/1998 | Lemelson | |
| 5,855,553 A | 1/1999 | Tajima et al. | |
| 5,855,583 A | 1/1999 | Wang et al. | |
| 5,860,992 A | 1/1999 | Daniel et al. | |
| 5,861,024 A | 1/1999 | Rashidi | |
| 5,868,755 A | 2/1999 | Kanner et al. | |
| 5,876,325 A | 3/1999 | Mizuno et al. | |
| 5,878,193 A | 3/1999 | Wang et al. | |
| 5,904,667 A | 5/1999 | Falwell | |
| 5,907,664 A | 5/1999 | Wang et al. | |
| 5,928,248 A | 7/1999 | Acker | |
| 5,931,832 A | 8/1999 | Jensen | |
| 5,950,629 A | 9/1999 | Taylor et al. | |
| 5,954,692 A | 9/1999 | Smith et al. | |
| 5,957,941 A | 9/1999 | Ream | |
| 5,964,717 A | 10/1999 | Gottlieb et al. | |
| 5,971,976 A | 10/1999 | Wang et al. | |
| 5,976,122 A | 11/1999 | Madhani et al. | |
| 6,001,108 A | 12/1999 | Wang et al. | |
| 6,004,271 A | 12/1999 | Moore | |
| 6,007,550 A | 12/1999 | Wang et al. | |
| 6,007,560 A | 12/1999 | Gottlieb et al. | |
| 6,024,695 A | 2/2000 | Taylor et al. | |
| 6,033,378 A | 3/2000 | Lundquist et al. | |
| 6,036,636 A | 3/2000 | Motoki et al. | |
| 6,058,323 A | 5/2000 | Lemelson | |
| 6,063,093 A | 5/2000 | Winston et al. | |
| 6,063,095 A | 5/2000 | Wang et al. | |
| 6,080,170 A | 6/2000 | Nash et al. | |
| 6,080,181 A | 6/2000 | Jensen et al. | |
| 6,083,170 A | 7/2000 | Ben-Haim | |
| 6,096,004 A | 8/2000 | Meglan et al. | |
| 6,102,850 A | 8/2000 | Wang et al. | |
| 6,102,920 A | 8/2000 | Sullivan et al. | |
| 6,106,511 A | 8/2000 | Jensen | |
| 6,120,433 A | 9/2000 | Mizuno et al. | |
| 6,126,635 A | 10/2000 | Simpson et al. | |
| 6,132,368 A | 10/2000 | Cooper | |
| 6,132,441 A | 10/2000 | Grace | |
| 6,146,355 A | 11/2000 | Biggs | |
| 6,156,005 A | 12/2000 | Theron | |
| 6,171,234 B1 | 1/2001 | White et al. | |
| 6,179,856 B1 | 1/2001 | Barbere | |
| 6,197,017 B1 | 3/2001 | Brock et al. | |
| 6,203,507 B1 * | 3/2001 | Wadsworth et al. | 600/585 |
| 6,203,525 B1 | 3/2001 | Whayne et al. | |
| 6,206,903 B1 | 3/2001 | Ramans | |
| 6,221,070 B1 | 4/2001 | Tu et al. | |
| 6,223,100 B1 | 4/2001 | Green | |
| 6,231,565 B1 | 5/2001 | Tovey et al. | |
| 6,233,504 B1 | 5/2001 | Das et al. | |
| 6,236,432 B1 | 5/2001 | Lee | |
| 6,245,020 B1 | 6/2001 | Moore et al. | |
| 6,246,200 B1 | 6/2001 | Blumenkranz et al. | |
| 6,267,781 B1 | 7/2001 | Tu | |
| 6,269,819 B1 | 8/2001 | Oz et al. | |
| 6,273,862 B1 * | 8/2001 | Privitera et al. | 600/568 |
| 6,283,921 B1 | 9/2001 | Nix et al. | |
| 6,287,297 B1 * | 9/2001 | Woodruff et al. | 606/7 |
| 6,290,675 B1 | 9/2001 | Vujanic et al. | |
| 6,292,681 B1 | 9/2001 | Moore | |
| 6,298,257 B1 | 10/2001 | Hall et al. | |
| 6,309,397 B1 | 10/2001 | Julian et al. | |
| 6,312,435 B1 | 11/2001 | Wallace et al. | |
| 6,319,227 B1 | 11/2001 | Mansouri-Ruiz | |
| 6,321,106 B1 | 11/2001 | Lemelson | |
| 6,325,808 B1 | 12/2001 | Bernard et al. | |
| 6,331,181 B1 | 12/2001 | Tierney et al. | |
| 6,332,889 B1 | 12/2001 | Sancoff et al. | |
| 6,346,072 B1 | 2/2002 | Cooper | |
| 6,352,503 B1 | 3/2002 | Matsui et al. | |

| | | |
|---|---|---|
| 6,364,888 B1 | 4/2002 | Niemeyer et al. |
| 6,369,834 B1 | 4/2002 | Zilles et al. |
| 6,371,907 B1 | 4/2002 | Hasegawa et al. |
| 6,371,952 B1 | 4/2002 | Madhani et al. |
| 6,375,471 B1 | 4/2002 | Wendlandt et al. |
| 6,377,011 B1 | 4/2002 | Ben-Ur |
| 6,385,509 B2 | 5/2002 | Das et al. |
| 6,394,998 B1 | 5/2002 | Wallace et al. |
| 6,397,323 B1 | 5/2002 | Yoshida |
| 6,398,726 B1 | 6/2002 | Ramans et al. |
| 6,398,755 B1 | 6/2002 | Belef et al. |
| 6,400,979 B1 | 6/2002 | Stoianovici et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 * | 10/2002 | Evans et al. .................... 606/1 |
| 6,485,489 B2 | 11/2002 | Teirstein et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,565,554 B1 | 5/2003 | Niemeyer |
| 6,569,084 B1 | 5/2003 | Mizuno et al. |
| 6,574,355 B2 | 6/2003 | Green |
| 6,587,750 B2 | 7/2003 | Gerbi et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,626,899 B2 | 9/2003 | Houser et al. |
| 6,645,196 B1 | 11/2003 | Nixon et al. |
| 6,659,939 B2 | 12/2003 | Moll et al. |
| 6,669,687 B1 | 12/2003 | Saadat |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,702,826 B2 | 3/2004 | Liddicoat et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,810,281 B2 | 10/2004 | Brock |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 | 1/2005 | Morley et al. |
| 6,843,793 B2 | 1/2005 | Brock |
| 6,852,107 B2 | 2/2005 | Wang et al. |
| 6,858,003 B2 | 2/2005 | Evans et al. |
| 6,860,877 B1 | 3/2005 | Sanchez et al. |
| 6,860,878 B2 | 3/2005 | Brock |
| 6,911,916 B1 | 6/2005 | Wang et al. |
| 6,936,001 B1 | 8/2005 | Snow |
| 6,936,056 B2 | 8/2005 | Nash et al. |
| 6,949,106 B2 | 9/2005 | Brock |
| 6,951,535 B2 | 10/2005 | Ghodoussi et al. |
| 6,963,792 B1 | 11/2005 | Green |
| 6,994,708 B2 | 2/2006 | Manzo |
| 6,997,931 B2 * | 2/2006 | Sauer et al. .................... 606/139 |
| 7,021,173 B2 | 4/2006 | Stoianovici et al. |
| 7,025,064 B2 | 4/2006 | Wang et al. |
| 7,074,179 B2 | 7/2006 | Wang et al. |
| 7,087,049 B2 | 8/2006 | Nowlin et al. |
| 7,090,683 B2 | 8/2006 | Brock et al. |
| 7,169,141 B2 | 1/2007 | Brock et al. |
| 7,214,230 B2 | 5/2007 | Brock et al. |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 2001/0031983 A1 | 10/2001 | Brock |
| 2002/0087151 A1 | 7/2002 | Mody et al. |
| 2002/0120252 A1 | 8/2002 | Brock |
| 2002/0128661 A1 | 9/2002 | Brock |
| 2002/0128662 A1 | 9/2002 | Brock |
| 2002/0138082 A1 | 9/2002 | Brock |
| 2003/0045888 A1 | 3/2003 | Brock |
| 2005/0203382 A1 | 9/2005 | Govari et al. |
| 2007/0060879 A1 | 3/2007 | Weitzner et al. |
| 2008/0300592 A1 | 12/2008 | Weitzner et al. |

FOREIGN PATENT DOCUMENTS

| | | |
|---|---|---|
| WO | WO 9314704 | 8/1993 |
| WO | WO 98/25666 | 6/1998 |
| WO | WO 9825666 | 6/1998 |
| WO | WO 00/60521 | 10/2000 |
| WO | WO 0060521 | 10/2000 |
| WO | WO 00/67640 | 11/2000 |
| WO | WO 02/74178 | 2/2002 |
| WO | WO 02051329 | 7/2002 |
| WO | WO 02074178 | 9/2002 |

OTHER PUBLICATIONS

M.W. Thring, "Robots and Telechirs: Manipulators With Memory; Remote Manipulators; Machine Limbs for the Handicapped", First published in 1983 by Ellis Horwood Limited.

* cited by examiner

CATHETER DRIVER SYSTEM

RELATED APPLICATIONS

This application claims the benefit of U.S. Provisional Application No. 60/332,287 filed Nov. 21, 2001, and is a continuation in part of U.S. application Ser. No. 10/216,067 filed Aug. 8, 2002 now abandoned, which claims the benefit of U.S. Provisional Application No. 60/313,497 filed Aug. 21, 2001, and is a continuation in part of U.S. application Ser. No. 10/023,024, now abandoned Ser. No. 10/011,371 now U.S. Pat. No. 7,090,683, Ser. No. 10/011,449, now abandoned Ser. No. 10/010,150 now U.S. Pat. No. 7,214,230, Ser. No. 10/022,038, now abandoned, Ser. No. 10/012,586 now U.S. Pat. No. 7,371,210, all filed Nov. 16, 2001, and all of which claim the benefit of U.S. Provisional Application Nos. 60/269,200 filed Feb. 15, 2001, 60/276,217 filed Mar. 15, 2001, 60/276,086 filed Mar. 15, 2001, 60/276,152 filed Mar. 15, 2001, and 60/293,346 filed May 24, 2001.

The entire teachings of the above applications are incorporated herein by reference.

BACKGROUND

Catheters are used extensively in the medical field in various types of medical procedures, as well as other invasive procedures. In general, minimally invasive medical procedures involve operating through a natural body opening or orifice of a body lumen, or through small incisions, typically 5 mm to 10 mm in length, through which instruments are inserted. In general, minimally invasive surgery is less traumatic than conventional surgery, due, in part, because no incision is required in certain minimally invasive procedures, or the significant reduction in the incision size in other procedures. Furthermore, hospitalization is reduced and recovery periods are shortened as compared with conventional surgical techniques.

Catheters may be provided in a variety of different shapes and sizes depending upon the particular application. It is typical for a clinician to manipulate the proximal end of the catheter to guide the distal end of the catheter inside the body, for example, through a vein or artery. Because of the small size of the incision or opening and the remote location of the distal end of the catheter, much of the procedure is not directly visible to the clinician. Although clinicians can have visual feedback from the procedure site through the use of a video camera or endoscope inserted into the patient, or through radiological imaging or ultrasonic imaging, the ability to control even relatively simple instruments remains difficult.

In some procedures, such as electrophysiology, the surgeon manually places the distal end of an extension, such as a catheter, at a site of interest in the patient's body. The distal end of the catheter can be coupled to an energy generator to treat the site of interest. Alternatively, or additionally, the catheter can be connected to a detector which receives signals from the distal end of the catheter for diagnostic purposes. The catheter is typically connected to a handle that includes control devices such as dials that enable the surgeon to articulate the catheter, and thus, to maneuver the catheter through the patient.

In view of the above, some have proposed using robotic tele-surgery to perform minimally invasive procedures. Typically, these robotic systems use arms that reach over the surgical table and manipulate the surgical instruments inserted into the patient, while the surgeon sits at a master station located a distance from the table and issues commands to the arms.

SUMMARY

An apparatus for performing medical procedures on an anatomical body includes an extension with an element near its distal end to be extended into the body, and a driver that moves the extension axially into the body, and that causes flexure of the distal end of the extension. The movement and flexure of the extension is driven by the driver from the proximal end of the extension, and an electronic controller directs the operation of the driver.

In some embodiments, the driver includes control devices which may include conventional handle dials. A first control device is coupled to a first control wire, and a second control device is coupled to a second control wire. The first and second control wires extend along the length of the extension, and the terminal ends of the first and second control wires are coupled to the distal end of the extension. The first and second control devices are operated to control the flexure movements of the distal end of the extension with at least two degrees-of-freedom. The first and second control devices can be part of a handle which is a plug-in module that is removable from the driver.

In certain embodiments, the driver moves the extension with a rotational movement. The driver may include a first drive mechanism and a second drive mechanism that are coupled to a motor array. The motor array in turn may be coupled to the controller, which directs the operation of the motor array and consequent operation of the drive mechanisms to move the extension with the axial and rotational movements.

In some embodiments, the element may receive RF energy from an RF generator for delivery to a target site in the body. In particular embodiments, the element provides signals from the target site to a detector. The signals are typically related to properties of the target site.

Since the movements of the driver are under the direction of the controller, these movements may be gentler than those produced by the surgeon when the instrument is manually driven through the patient. Furthermore, with the assistance of the driver, the surgeon is less likely to become fatigued during the procedure.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention provides a drive system that can be used to manipulate a surgical implement from its proximal end. For example, a manually operable instrument can be coupled to the drive system without requiring any modification to the instrument. The drive system can be operated by a surgeon at a master station of a master-slave telerobotic system. In some embodiments, the drive apparatus is in the form of a housing in which the instrument is inserted, which is then driven as the surgeon manipulates the housing.

Figure 1:
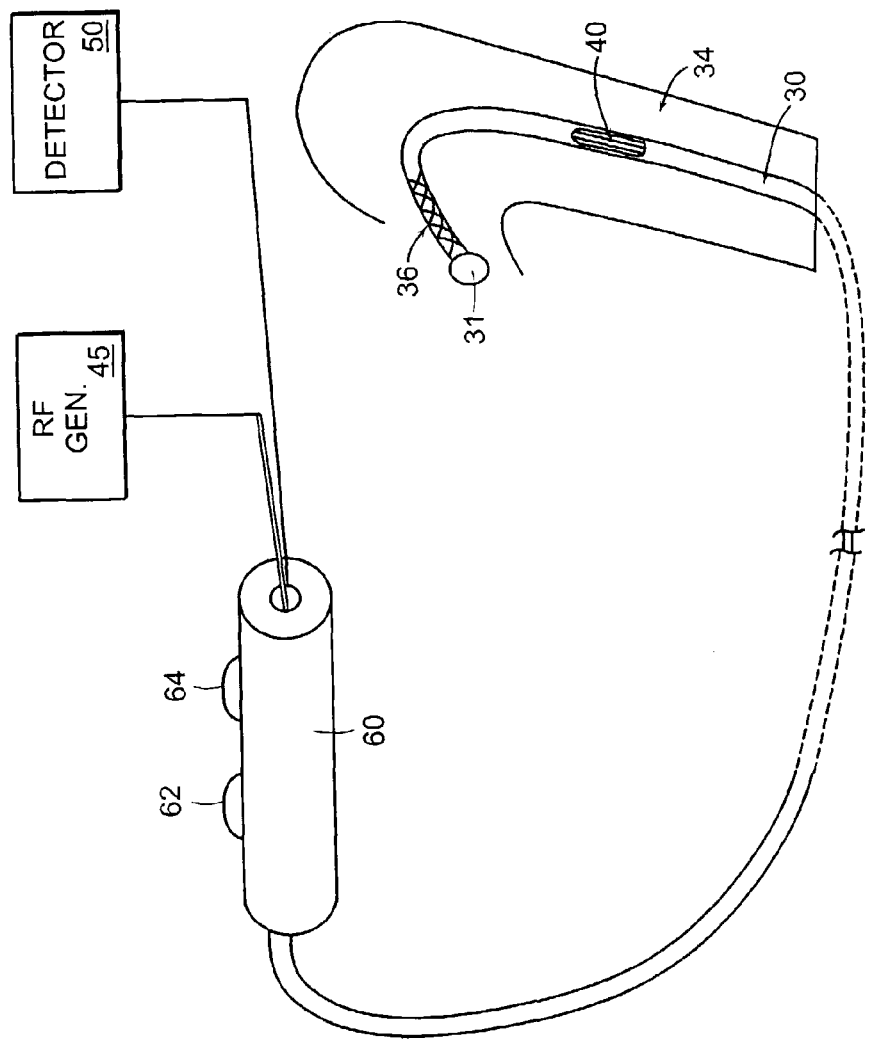
FIG. 1 illustrates a manual catheter system.
Figure 1A:
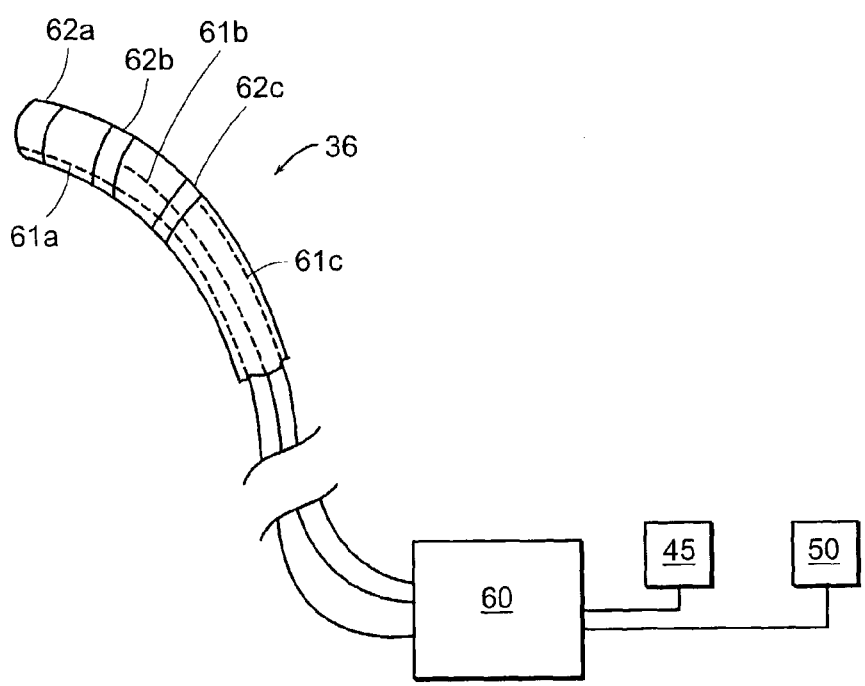
FIG. 1A a close-up view of the terminal end of the catheter shown in FIG. 2.

In electrophysiology procedures, as shown in FIG. 1, a extension such as a catheter 30 is used for diagnostic purposes or sensing conditions at a predetermined target site 31 as the catheter 30 extends through an artery or vein 34. The distal end 36 of the catheter 30 can be considered as an operative segment of the catheter and thus is capable of flexing or bending to assist guiding the catheter through the anatomic body, and curving to a desired location, for example, to lean against an inner surface of the heart. In this regard, there is schematically illustrated wiring 40 that may extend along the length of the catheter 30 that transmits mechanical inputs of a manual handle 60. As shown in FIG. 1A, there can be additional wiring 61a, 61b, and 61c that are connected to respective electrophysiology elements 62a, 62b, and 62c and extend from the distal end 36 to an RF generator 45, as well as a detector 50, associated with the handle 60 (FIG. 1).

In some embodiments, the RF generator 45 couples energy through the handle 60 by way of the catheter 30 to the elements 62a, 62b, and 62c at the distal end 36 for the application of RF energy at the target site 31 for therapeutic purposes. In association with the RF generator 45, the detector 50 may receives signals from a probe, such as the elements 62a, 62b, and 62c, positioned at the target site. Typically, these signals are related to physiological properties at the target site.

As can be seen in FIG. 1, the handle 60 has wheels or dials 62 and 64 that can be manually operated by the surgeon during a procedure. Manipulation of the dials 62 and 64 are transmitted through the control wiring 40 to the distal end 36 to control the flexing or bending of the distal end in respective orthogonal directions.

Figure 2:
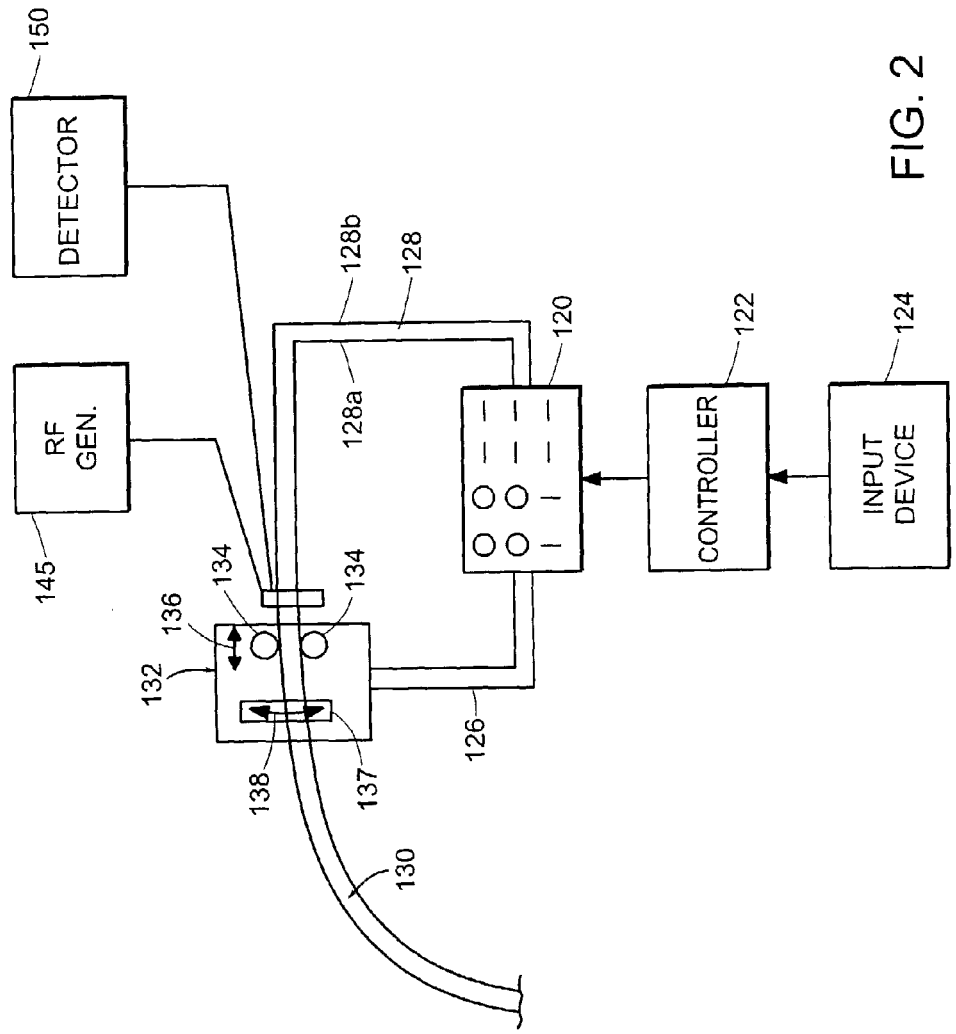
FIG. 2 is a block and schematic diagram of a catheter drive system in accordance with the present invention.

In a particular embodiment, as shown in FIG. 2, the operation of the drive system of FIG. 1 is automated. That is, the system shown in FIG. 2 modifies the construction of that shown in FIG. 1 by providing for automatic control of a catheter 130, which at its distal end is substantially the same as the catheter 30 shown in FIGS. 1 and 1A.

Like the catheter 30, the catheter 130 is able to move at its end with at least two degrees-of-freedom under control of wires 128a and 128b. In addition, the catheter 130 is coupled at its distal end to a support block 132 that includes wheels 134 that provide linear translation of the catheter 130 in the direction 136. A further mechanism 137 provides rotational motion of the catheter 130, such as depicted by the arrow 138. Moreover, there are also wires extending through the catheter 130 associated with the RF generator 145 and the detector 150.

In the embodiment illustrated in FIG. 2, a guide wire is not used, nor is a guide wire used in the device shown in FIGS. 1 and 1A. Accordingly, only a single support block 132 is used with this catheter construction. However, the particular catheter 130 is provided with the flex control, and hence is provided with control wires that extend through the catheter 130 like those described previously in reference with FIG. 1.

As shown in FIG. 2, the support or drive block 132 is coupled to an electromechanical drive member or motor array 120. Also included in the system is an input device 124 at which a surgeon provides control actuations. The input device 124 is coupled to a controller 122 which in turn is coupled to the motor array 120. Thus, instructions from the input device 124 are received by the controller 122 which then directs the operation of the motor array 120.

As mentioned previously, movement of the motors of the array 120 is transmitted to the catheter 130 through mechanically cabling extending through the catheter. In particular, a mechanical cabling 126 coupled directly to the block 132 controls the rotational and linear degrees-of-freedom of the catheter 130 through the mechanism 137 and wheels 134, respectively. In addition, there is a cabling 128 from the motor array 120 to the block 132 which controls the bending and flexing movement of the catheter 130. As such, one cable 128a may be used to control the bending movements of the catheter with one degree-of-freedom, and another cable 128b may control the bending movements with a second degree-of-freedom.

The input device 124 may include separate manipulators for the different movements of the catheter 130. As described in connection with FIG. 1, the input device can take on one of many different forms including joysticks, wheels, dials, and other types of manual interfaces. For the control desired in FIG. 2, one input member controls the mechanical cabling 126 for providing the two degrees-of-freedom of action of the catheter 130, in particular, the linear and rotational movement. Another input member in input device 124 controls the flexing and bending of the catheter 130 by way of the mechanical cabling 128. The input instructions from the input device 124 are transmitted to the motor array 120 by way of the controller 122 which may be a microprocessor.

Figure 2A:
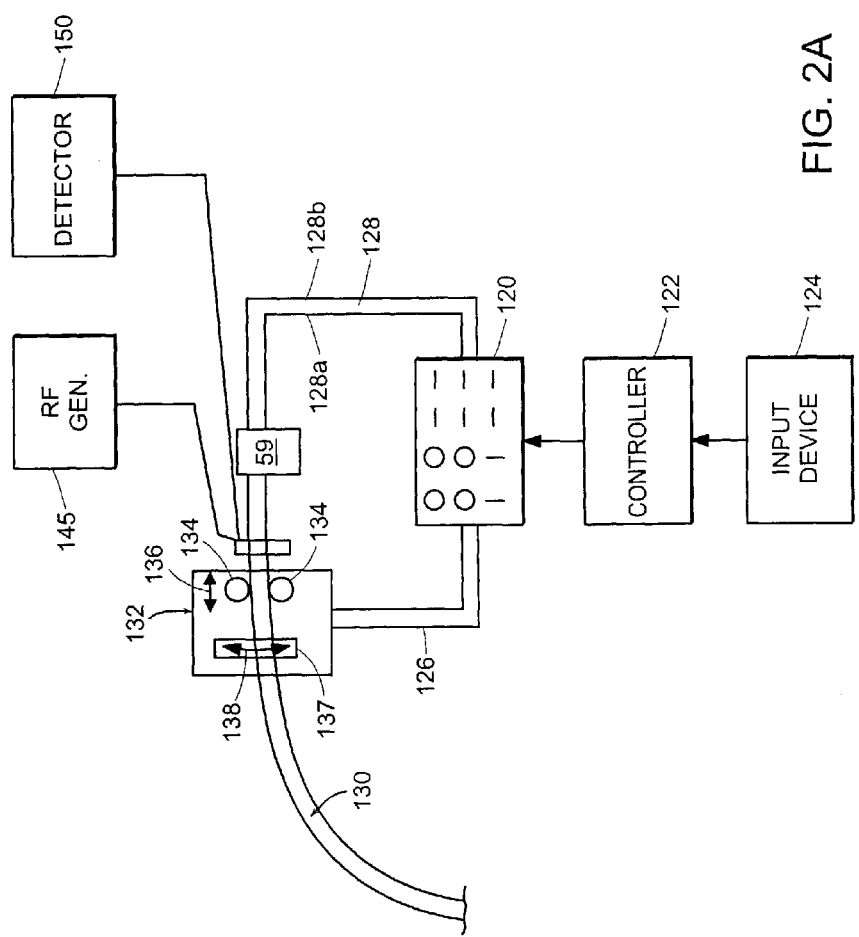
FIG. 2A is a variation of the configuration shown in FIG. 3.

In an alternative arrangement, as shown in FIG. 2A, an intermediate drive device 59 may be interposed between the motor array 120 and the catheter 130. In such an arrangement, the motor array 120 communicates with the drive device 59 over the lines 128, which may be electrical. In turn, the drive device 59 is coupled to the cabling extending through the length of the catheter, and actuates the cabling to cause the distal end of the catheter 130 to bend and flex with one or more degrees-of-freedom.

Details of an automated catheter drive system are describe in the U.S. Application entitled "Coaxial Catheter System," by Weitzer, Rogers, and Solbjor, Ser. No. 10/270,740, filed herewith, the entire contents of which are incorporated herein by reference. Details of a imaging system that aids the movement of the catheter through an anatomic body are describe in the U.S. Application entitled "Catheter Tracking System," by Weitzner and Lee, Ser. No. 10/216,669, filed herewith, the entire contents of which are incorporated herein by reference.

Figure 3:
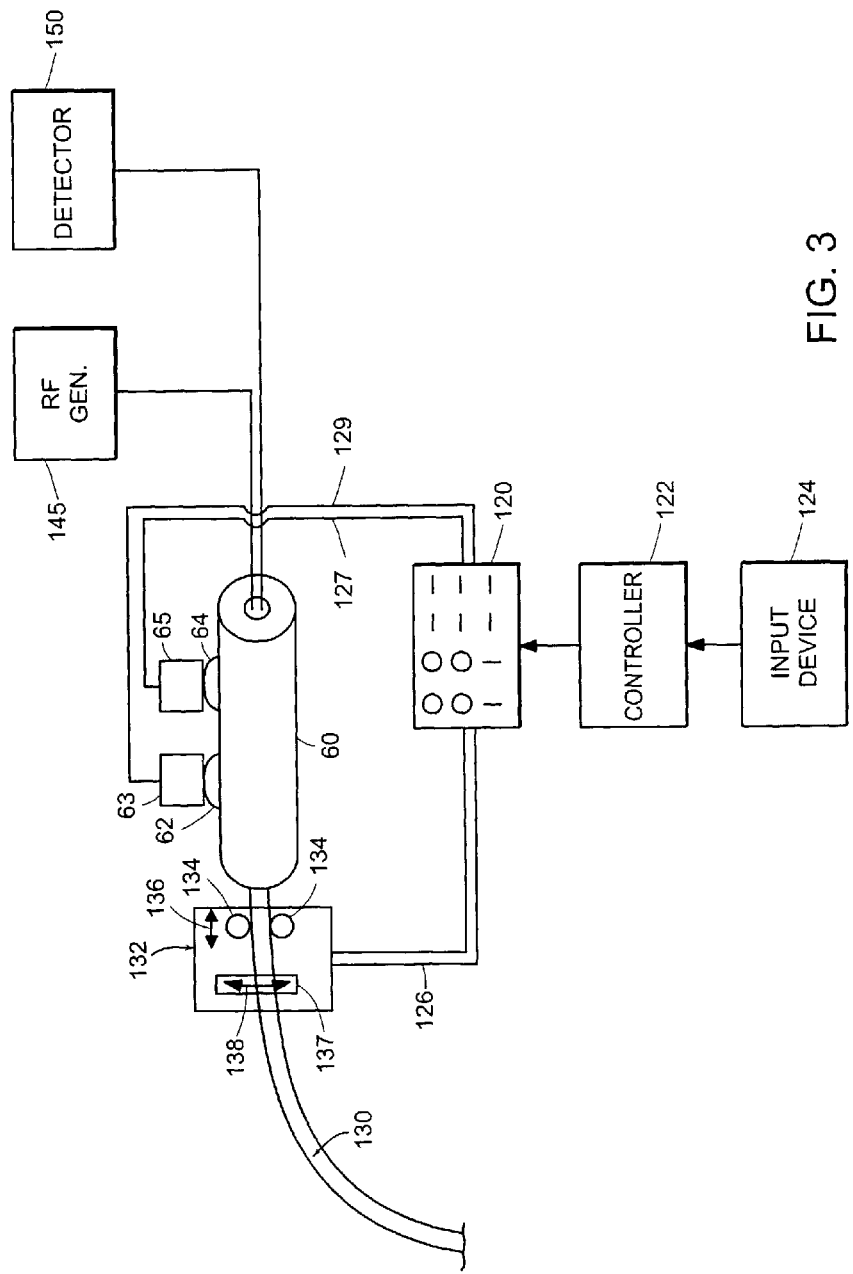
FIG. 3 is a block and schematic diagram of another version of a catheter drive system in accordance with the present invention.

Referring now to FIG. 3, there is shown a further embodiment of a catheter drive system. In FIG. 3, like reference characters are used to identify like features shown in FIG. 2. Thus, in the embodiment of FIG. 3, there is an input device 124, a controller 122, and a motor array 120. FIG. 3 also depicts the support block 132 which provides both linear and rotational movement of the catheter 130. As before, these movements are provide by wheels 134 for the linear translation as noted by the arrow 136, and the member or mechanism 137 for the rotational translation as noted by the arrow 138.

In the embodiment of FIG. 3, the handle 60 is depicted with its pair of actuating wheels or dials 62 and 64 shown earlier in FIG. 1. Rather than replacing the handle 60, as in the embodiment of FIG. 2, the handle 60 here remains intact so that the wheels 62 and 64 are used to control the flexing and bending of the catheter 130. For this purpose, there are included drive pieces 63 and 65 associated, respectively, with the wheels 62 and 64. Each of the drive pieces engages its corresponding wheel to drive the wheels in either direction to provide the appropriate flex control of the catheter 130. Note in FIG. 3, the separate lines 127 and 129, which may be mechanical or electrical, coupling the drive pieces 65 and 63 to the motor array 120. Hence, actuation of respective drive units in the motor array 120 results in a consequent actuation of the wheels 62 and 64 via the control line 129 and drive piece 63, and the control line 127 and drive piece 65, respectively. Note that with this embodiment the proper support and housings are provided such that the drive pieces 63 and 65 maintain proper engagement with the wheels 62 and 64.

With the particular arrangement shown in FIG. 3, the existing catheter construction need not be modified. Rather, the drive system shown in FIG. 3 is simply coupled to an existing catheter system, such as the handle 60 and catheter 130 combination.

Although the motor array 120 is illustrated as having two separate lines for two separate drive pieces, in other embodiments, the handle 60 may have only a single control dial. In such implementations, there may be only a single line and associated drive piece that couples the motor array 120 to the handle 60. Thus, unlike the handle 60 with wheels 62 and 64 which provide flex control in orthogonal planes, if only a single wheel is used, the catheter typically flexes only in a single plane. However, in arrangements in which the catheter support block 132 provides for rotational movement of the catheter 130, the movement of the catheter is not limited to this single plane, since as the catheter is being rotated it moves out of this plane.

Figure 4:
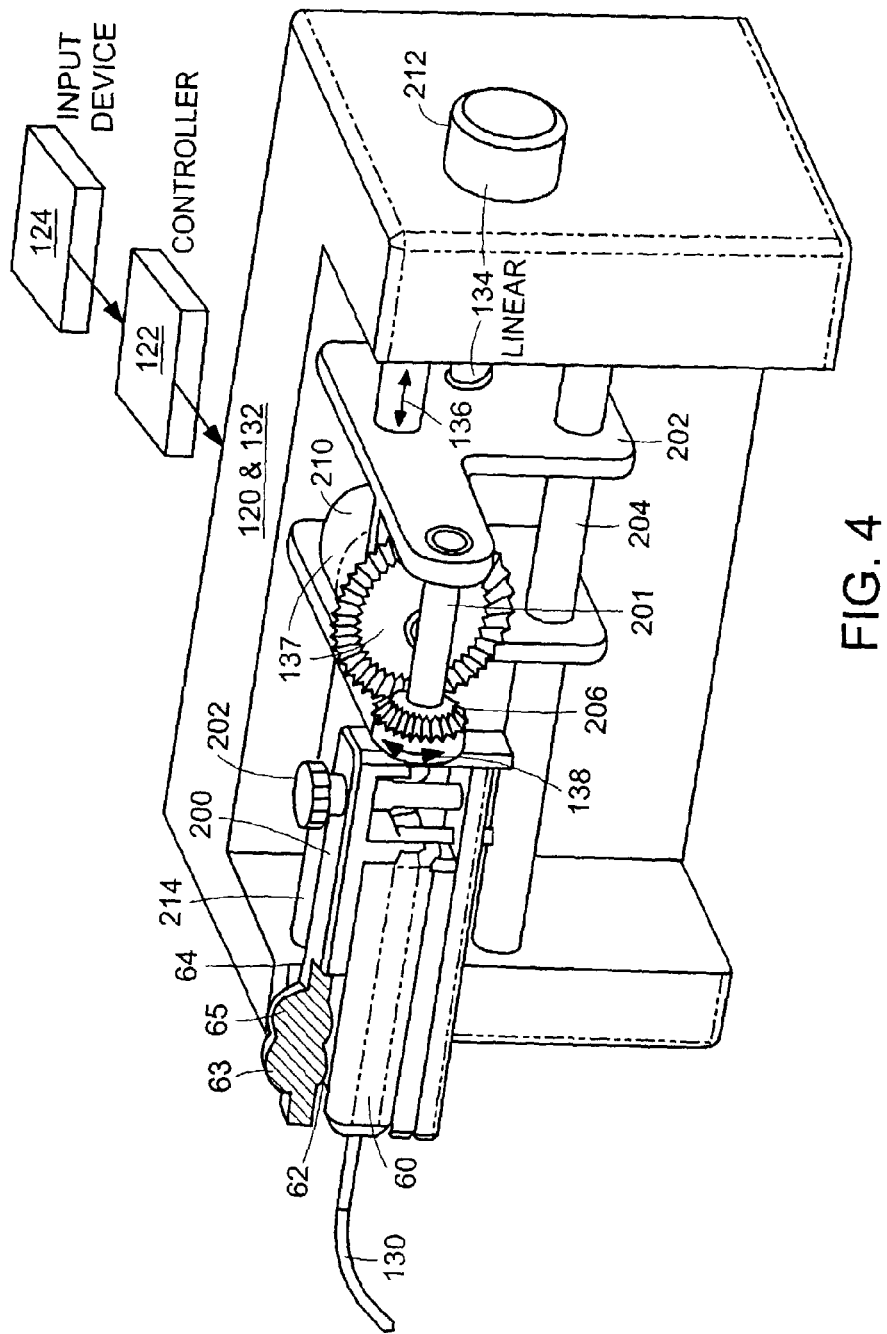
FIG. 4 is a perspective view of an illustrative embodiment of the catheter drive system of FIG. 3.
Figure 4A:
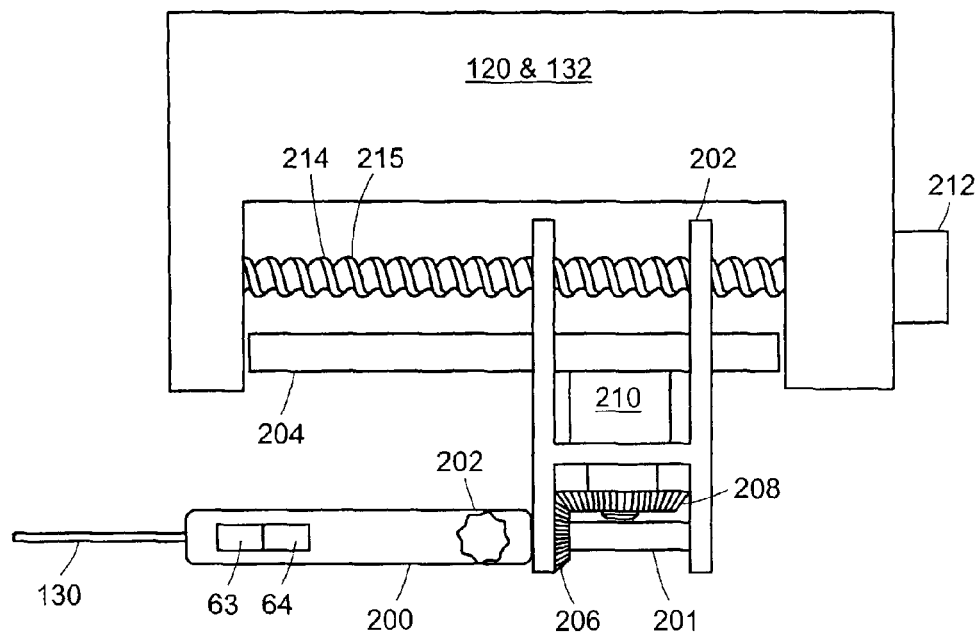
FIG. 4A is a top view of the catheter drive system of FIG. 4.
Figure 4B:
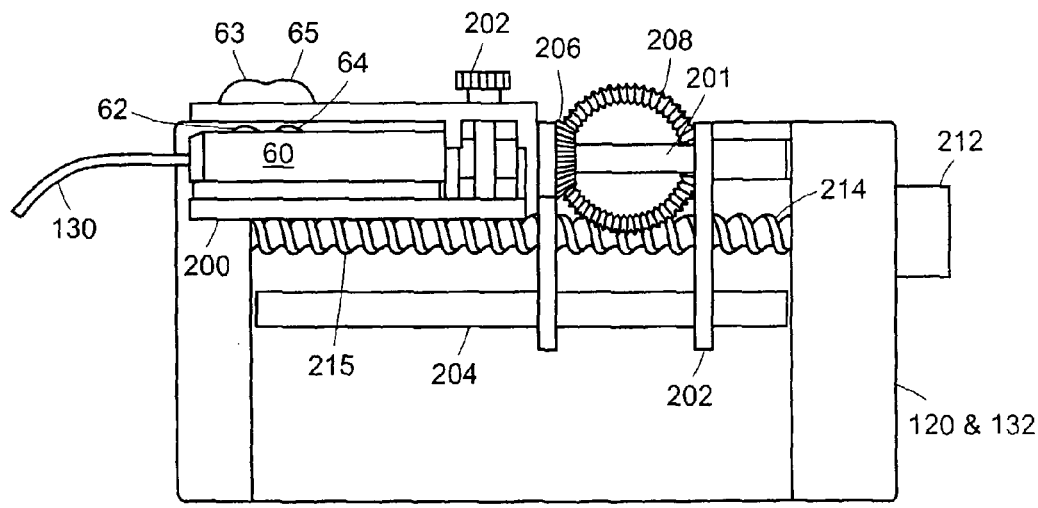
FIG. 4B is a front view of the catheter drive system of FIG. 4.

A particular embodiment of the system of FIG. 3 is illustrated in FIGS. 4, 4A, and 4B, where like reference characters are used to identify like features shown in FIG. 3. In this embodiment, the handle 60 is clamped in a clamp or vise 200 with a screw 202. The clamp 200 is connected to a shaft 201 supported in a carriage 202 that moves back and forth on a guide bar 204 mounted in the drive block 132. Associated with the shaft 201 is a set of gears 206 that engage with another set of gears 208 of the rotary drive mechanism 137. The drive mechanism 137 includes a motor 210 driven by the array 120 located in the drive block 132 and under the direction of the controller 122 as it receives instructions from the user through the input device 124. Thus, as the motor 210 rotates the gears 208, a consequent rotary motion is induced in the gears 206 to rotate the clamp 200, and hence the handle 60 and catheter 130, in the rotational direction 138.

The linear drive mechanism 134 of this embodiment includes a motor 212 connected to a screw drive 214. The motor 212 and screw drive 214 are mounted to the drive block 132 in a manner to allow the screw drive 214 to rotate. The screw drive 214 has threads 215 about its periphery that engage with the carriage 202. Accordingly, under the direction of the controller 122 via the array 120, the motor 212 rotates the screw drive 214 to induce the carriage 202, and hence the handle 60 and catheter 130, to move back and forth in the linear direction 136.

As previously mentioned, the drive pieces 63 and 65 engage with the dials or wheels 62 and 64 of the handle 60 so that upon instructions from the user through the input device 124, the drive pieces 63 and 65 manipulate the dials 62 and 64 to control the desired bending and flexing movements of the catheter 130.

This invention can be implemented and combined with other applications, systems, and apparatuses, for example, those discussed in greater detail in U.S. Provisional Application No. 60/332,287, filed Nov. 21, 2001, the entire contents of which are incorporated herein by reference, as well as those discussed in greater detail in each of the following documents, all of which are incorporated herein by reference in their entirety:

U.S. application Ser. No. 09/783,637 filed Feb. 14, 2001, which is a continuation of PCT application Serial No. PCT/US00/12553 filed May 9, 2000, which claims the benefit of U.S. Provisional Application No. 60/133,407 filed May 10, 1999; U.S. Application entitled "Articulated Apparatus for Telemanipulator System," by Brock and Lee, Ser. No. 10/208,087, filed Jul. 29, 2002, which is a continuation of U.S. application Ser. No. 09/827,503 filed Apr. 6, 2001, which is a continuation of U.S. application Ser. No. 09/746,853 filed Dec. 21, 2000, which is a divisional of U.S. application Ser. No. 09/375,666 filed Aug. 17, 1999, now U.S. Pat. No. 6,197,017 which issued on Mar. 6, 2001, which is a continuation of U.S. application Ser. No. 09/028,550 filed Feb. 24, 1998, which is now abandoned; PCT application Serial No. PCT/US01/11376 filed Apr. 6, 2001, which claims priority to U.S. application Ser. No. 09/746,853 filed Dec. 21, 2000, and U.S. application Ser. No. 09/827,503 filed Apr. 6, 2001; U.S. application Ser. Nos. 10/014,143, 10/012,845, 10/008,964, 10/013,046, 10/011,450, 10/008,457, and 10/008,871, all filed Nov. 16, 2001 and all of which claim benefit to U.S. Provisional Application No. 60/279,087 filed Mar. 27, 2001; U.S. application Ser. No. 10/077,233 filed Feb. 15, 2002, which claims the benefit of U.S. Provisional Application No. 60/269,203 filed Feb. 15, 2001; U.S. application Ser. No. 10/097,923 filed Mar. 15, 2002, which claims the benefit of U.S. Provisional Application No. 60/276,151 filed Mar. 15, 2001; U.S. application Ser. No. 10/034,871 filed Dec. 21, 2001, which claims the benefit of U.S. Provisional Application No. 60/257,816 filed Dec. 21, 2000; U.S. application Ser. No. 09/827,643 filed Apr. 6, 2001, which claims the benefit of U.S. Provisional Application No. 60/257,869 filed Dec. 21, 2000, and U.S. Provisional Application No. 60/195,264 filed Apr. 7, 2000.

While this invention has been particularly shown and described with references to preferred embodiments thereof, it will be understood by those skilled in the art that various changes in form and details may be made therein without departing from the scope of the invention encompassed by the appended claims. For example, the catheter need not be limited for use in electrophysiology procedures. That is, there may be other types of probes or end effectors located at the distal end of the catheter. The end effector may be, for example, an articulated tool such a grasper, scissor, needle holder, micro dissector, staple applier, tacker, suction irrigation tool, and clip applier. The end effector can also be a non-articulated tool, such as a cutting blade, probe, irrigator, catheter or suction orifice, and dilation balloon.

What is claimed is:

1. A medical system, comprising:
  a medical probe including an elongated body having a proximal end and a distal end, one or more operative elements carried by the distal end of the elongated body, a probe handle mounted to the proximal end of the elongated body, wherein a control element on the probe handle is operatively coupled with a steering mechanism located in the probe handle, and wherein mechanical manipulation of the control element on the probe handle causes corresponding movement of the distal end of the elongated body by the steering mechanism;

a user input device configured for generating user signals corresponding to a desired movement of the distal end of the elongated body in response to a user actuation of the user input device;

an electronic controller configured for generating electrical control signals corresponding to a mechanical manipulation of the control element in response to the user signals generated by the user input device; and a probe driver configured for removable mounting of the probe handle and for interfacing with the control element on the probe handle to mechanically manipulate the control element in response to the control signals generated by the electronic controller, thereby causing corresponding movement of the distal end of the elongated body.

2. The medical system of claim 1, wherein the elongated body is flexible.

3. The medical system of claim 1, wherein the elongated body is configured for being introduced through a blood vessel.

4. The medical system of claim 1, wherein the user input device comprises one or more of a joystick, wheel, or dial.

5. The medical system of claim 1, wherein mechanical manipulation of the control element on the probe handle causes corresponding movement of the distal end of the elongated body in a plurality of degrees-of-freedom.

6. The medical system of claim 1, wherein mechanical manipulation of the control element on the probe handle causes a flexure of the distal end of the elongated body.

7. The medical system of claim 6, wherein the flexure is bi-directional in a single plane.

8. The medical system of claim 6, wherein the flexure is in orthogonal planes.

9. The medical system of claim 1, wherein the driver is configured for axially translating the elongated body in response to the electrical control signals generated by the electrical controller.

10. The medical system of claim 1, wherein the driver is configured for rotating the elongated body about a longitudinal axis in response to the electrical control signals generated by the electrical controller.

11. The medical system of claim 1, wherein the driver includes a drive mechanism configured for interfacing with the control element, and one or more motors coupled between the drive mechanism and the electrical controller.

12. The medical system of claim 1, wherein the control element comprises at least one dial.

13. The medical system of claim 9, wherein the driver includes a drive block and a carriage slidably mounted to the block, and wherein the probe handle is removably mounted to the carriage.

14. The medical system of claim 13, wherein the driver further includes a guide bar mounted to the drive block, and the carriage is configured for moving back and forth along the guide bar in a linear direction.

15. The medical system of claim 14, wherein the driver further includes a drive screw rotatably mounted to the drive block, the drive screw having threads that engage the carriage, wherein axial rotation of the drive screw moves the carriage back and forth along the guide bar in the linear direction.

16. The medical system of claim 15, further comprising a motor mounted to the drive block, the motor configured for rotating the drive screw relative to the drive block.

17. The medical system of claim 10, wherein the driver further includes a clamp in which the probe handle is removably mounted, a shaft mounted to the clamp, and a gear mounted to the shaft, wherein rotation of the gear rotates the probe handle and, thus, the elongated member about the longitudinal axis.

18. The medical system of claim 7, wherein the driver includes one or more drive pieces that directly interface with the control element to flex the distal end of the elongated body.

19. A medical system, comprising:

a medical probe including an elongated body having a proximal end and a distal end, one or more operative elements carried by the distal end of the elongated body, a probe handle mounted to the proximal end of the elongated body, and a control element on the probe handle and operatively coupled with a steering mechanism in the probe handle, wherein the control element is manually manipulable, and a manual manipulation of the control element on the probe handle causes corresponding movement of the distal end of the elongated body by the steering mechanism;

a user input device configured for generating user signals corresponding to a desired movement of the distal end of the elongated body in response to a user actuation of the user input device;

an electronic controller configured for generating electrical control signals corresponding to a mechanical manipulation of the control element in response to the user signals generated by the user input device; and a probe driver configured for removable mounting of the probe handle and for interfacing with the control element on the probe handle to mechanically manipulate the control element in response to the control signals generated by the electronic controller, thereby causing corresponding movement of the distal end of the elongated body without any manual manipulation of the control element on the probe handle.

* * * * *